United States Patent [19]

Otterbacher

[11] Patent Number: 4,528,394

[45] Date of Patent: Jul. 9, 1985

[54] PREPARATION OF HYDROXYAROMATIC ETHERS

[75] Inventor: Eric W. Otterbacher, Midland, Mich.

[73] Assignee: The Dow Chemical Company, Midland, Mich.

[21] Appl. No.: 519,794

[22] Filed: Aug. 3, 1983

[51] Int. Cl.³ .............................................. C07C 69/76
[52] U.S. Cl. .................................... 560/061; 568/650; 260/465 F; 562/606; 562/609
[58] Field of Search ......................... 560/61; 568/650; 260/465 F; 562/606, 609

[56] References Cited

U.S. PATENT DOCUMENTS

| 3,976,702 | 8/1976 | Suzuki et al. | 260/621 R |
| 4,051,318 | 9/1977 | Suzuki et al. | 560/131 |
| 4,169,720 | 10/1979 | Schacht et al. | 71/108 |
| 4,174,460 | 11/1979 | Seifert et al. | 560/61 |

FOREIGN PATENT DOCUMENTS 1599121  9/1981  United Kingdom .

OTHER PUBLICATIONS

*Am. Chem. Journal*, vol. 42, p. 477, (1909).
*Quarterly Review*, vol. 21, p. 454, (1967).

*Primary Examiner*—Paul J. Killos
*Attorney, Agent, or Firm*—Paul D. Hayhurst

[57] ABSTRACT

Prepare hydroxyaromatic ethers by contacting an oxidizing agent with an acylaromatic ether in the presence of an acid catalyst.

20 Claims, No Drawings

PREPARATION OF HYDROXYAROMATIC ETHERS

BACKGROUND OF THE INVENTION

Hydroxyaromatic ethers, such as the mono-substituted hydroquinones, resorcinols and catechols are generally difficult to prepare in high purity due to the complex separation of mono-, di- and unsubstituted dihydroxybenzenes. In traditional attempts to minimize this problem, low conversions are required. As a result, the cost of manufacturing the desired product is raised.

Hydroxyaromatic ethers are well known as polymerization inhibitors and as antioxidants. The monomethyl ether of hydroquinone is of significant economic importance. Additionally, the use of compounds such as methyl 2-(4-hydroxyphenoxy)propionate has been described in the patent literature as a building block to prepare a wide range of biologically active materials, especially herbicides. See, for example, European Patent No. 483 and British Patent Specifications Nos. 1,599,121 and 1,550,574.

U.S. Pat. No. 3,976,702 discloses the preparation of phenolic compounds, having from one to five alkyl substituents, via reacting the corresponding alkyl-substituted, formylbenzene with hydrogen peroxide in the presence of a solvent and a large amount of hydrofluoric acid at a temperature of from −50° C. to 50° C. in order to form an intermediate formyloxybenzene which is then heated in the presence of water to give the corresponding alkyl-substituted phenolic compounds. Similarly, U.S. Pat. No. 4,051,318 discloses the preparation of alkyl-substituted formyloxybenzenes, having lower alkyl substituents via reacting the corresponding alkyl-substituted formylbenzenes with certain carboxylic peracids in the presence of a solvent and a large amount of hydrofluoric acid at a temperature of from −50° C. to about 50° C.

The prior art does not disclose oxidation of substituted acylaromatic compounds where one or more of the substituents are not lower alkyl. Furthermore, the prior art does not disclose the use of only catalytic amounts of a strong acid. Instead, greater than stoichiometric amounts of hydrofluoric acid are specified. In view of these deficiencies, it would be desirable to have a process for the oxidation of substituted acylaromatic compounds having substituents which are different than lower alkyl so that, for example, hydroxyphenyl ethers could be produced. Additionally, it would be economically desirable to have a process which did not require large excesses of hydrofluoric acid.

SUMMARY OF THE INVENTION

The present invention is such a process, and it provides for the efficient and selective preparation of hydroxyaromatic ethers via the reaction of an acylaromatic ether with an oxidizing agent in the presence of a catalytic amount of an acid catalyst. Surprisingly, the oxidation of the present invention is selective to the aldehyde moiety in spite of the simultaneous presence of an oxidizable alkoxy moiety and an oxidizing agent. Further, the present invention is surprising in that a catalytic amount of an acid is employed as opposed to a large excess of hydrofluoric acid.

DETAILED DESCRIPTION OF THE INVENTION

In the practice of the present invention, it is essential to employ an oxidizing agent, an acid, and an acylaromatic ether. A solvent is optionally employed.

A preferred embodiment of the process of the present invention may be schematically represented as follows:

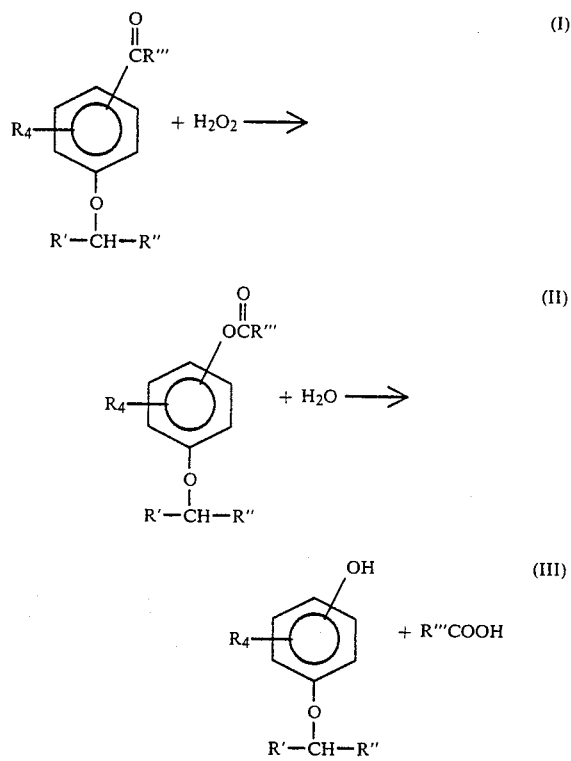

In view of the fact that the water, which is needed for second reaction of the preceding sequence, is produced as a product of the first reaction, the preceding sequence may be written as:

$$(I) + H_2O_2 \rightarrow (III) + R'''COOH.$$

In the preceding reactions, R is independently selected from H, halo, nitro, alkoxy, —CN, or lower alkyl; R' represents H, lower alkyl, alkoxy, or —CN; R''' represents H or lower alkyl; and R'' represents H, lower alkyl, —CN or carboxyl, the carboxyl moiety being represented generally by the formula:

wherein R'''' represents H, lower alkyl or a glycol ether.

The acylaromatic ether employed in the process of the present invention may be represented generally by Formula I, as described hereinbefore. Preferably, R and R''' are H, R' is H or lower alkyl, and R'' is H or a carboxyl moiety represent generally by the formula:

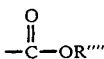

wherein R'''' is as described hereinbefore. Preferably R'''' is lower alkyl; most preferably R'''' is methyl. It is preferred to employ acylaromatic ethers in which the aromatic moiety is phenyl. When the aromatic moiety is phenyl, it is preferred that the acyl moiety and the moiety which bears R' be ortho or para with respect to each other, with para being most preferred. The preferred acyl moiety is formyl. Mixtures of acylaromatic ethers may be employed.

The oxidizing agent employed in the process of the present invention may be almost any compound which will oxidize the acylaromatic bond such that the acyl carbon atom which is bonded to the aromatic ring is displaced from the ring and replaced by an oxygen atom. Typical oxidizing agents include those compounds which bear a peroxide, —O—O—, moiety. Preferred oxidizing agents are represented generally by the formula:

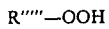
R'''''—OOH     (IV)

wherein R''''' is alkyl, aralkyl, acyl or H. Examples of preferred oxidizing agents include hydrogen peroxide, peracetic acid, t-butyl hydroperoxide, cumyl hydroperoxide, isopropylbenzene hydroperoxide and ethylbenzene hydroperoxide. Preferably R''''' is lower alkyl or H. The most preferred oxidizing agent is hydrogen peroxide, $H_2O_2$. The oxidizing agent is employed in an amount which is sufficient to oxidize the acylaromatic bond such that the acyl carbon atom which is bonded to the aromatic ring is displaced from the aromatic ring and replaced by an oxygen atom. Typically, from about 0.5 to about 5 equivalents of oxidizing agent are employed per equivalent of acylaromatic ether. Preferably from about 0.9 to about 1.5 equivalents of oxidizing agent are employed. While the oxidizing agent may be employed in pure, undiluted form, it is preferred to employ the oxidizing agent in diluted form. The preferred diluent is water. When the oxidizing agent is $H_2O_2$, it is preferred to employ approximately 10–90 weight percent $H_2O_2$ with water as the diluent. It is more preferred to employ aqueous $H_2O_2$ having a concentration of from about 30 to about 50 weight percent $H_2O_2$.

The acid is employed as a catalyst, and is employed in a catalytic amount. The acid generally increases the rate of the reaction and allows the reaction to proceed at lower temperatures. Typically, from about 0.001 to about 1 equivalent of acid is employed per equivalent of acylaromatic ether. Preferably, from about 0.05 to about 0.5 equivalents of acid are employed. The acid may be any acid which is strong enough to catalyze the reaction. Examples of acids which may be employed include hydrochloric, sulfuric, hydrofluoric, phosphoric, trifluoroacetic, and p-toluene sulfonic acid. Sulfuric acid is the preferred acid.

A solvent is optionally employed in the practice of the present invention. Solvents employed in the process of the present invention preferably are compounds having at least one oxygen atom therein, such as, for example, water, ethers, esters, ketones, alcohols and carboxylic acids. Specific examples of preferred solvents include methanol, ethanol, diethyl ether, ethyl acetate and acetic acid. Typically, from about 0 to about 50 volumes of solvent are employed per volume of acylaromatic ether. Preferably from about 0.5 to about 10 volumes of solvent are employed per volume of acylaromatic ether.

The temperature and pressure employed in the process of the present invention are not especially critical. The temperature typically ranges from about the freezing point to about the boiling point of the reaction mixture. Preferably, the temperature ranges from about 0° C. to about 100° C. The most preferred temperature range is from about 30° C. to about 80° C. The process may be operated at sub- or superatmospheric pressures, although it is preferred to operate at ambient pressure for the sake of convenience.

A continuous process wherein heat is removed as it is generated by the reaction is preferred. When hydrolyzable groups are present, it is desirable that the reaction be terminated before significant hydrolysis occurs. The reaction typically is complete within 0.1–100 hours of the starting time, and preferably is complete within about 0.1 to about 4 hours.

When an acylaromatic ether is reacted with an oxidizing agent as described hereinabove, a hydroxyaromatic ether is formed. Preferred hydroxyaromatic ether products are represented generally by the formula:

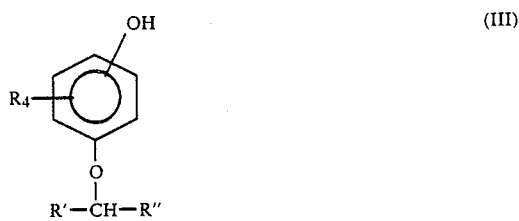
(III)

wherein R, R', and R" are as defined hereinabove. The product may be recovered using well-known techniques such as, for example, extraction, distillation and crystallization.

SPECIFIC EMBODIMENTS

The following preparations and examples are given to illustrate the invention and should not be construed as limiting its scope. All parts and percentages are by weight unless otherwise indicated.

Preparation of a Starting Material: Methyl 2-(4-formylphenoxy)propanoate

A 122.1-g portion of p-hydroxybenzaldehyde is dissolved in 500 ml dimethylsulfoxide (DMSO). An equimolar amount of aqueous 50 percent NaOH solution is added. The reaction mixture is heated under reduced pressure to remove water and DMSO overhead at up to 123° C. head temperature at 100 torr pressure. The reaction mixture is cooled to about 45° C. and methyl 2-chloropropanoate (128.7 g) is added. The reaction mixture is stirred at about 75° C. -80° C. for about 2 hours and is then poured into 400 ml $CH_2Cl_2$ and 400 ml water. The combined organic layer is washed with two 100-ml portions of water and is dried with $Na_2SO_4$. Removal of the solvent gives 213 g of a brown liquid. Distillation gives 122 g of methyl 2-(4-formylphenoxy)propanoate, which has a boiling point of 163° C. at 7 torr.

Example 1—Methyl 2-(4-hydroxyphenoxy)propanoate

A solution of 5.0 g of methyl 2-(4-formylphenoxy)propanoate in 15 ml methanol is added to a reactor over a period of about five minutes. Simultaneously, a solution of 1.8 g of aqueous 50 percent $H_2O_2$ and 0.24 g of 98 percent $H_2SO_4$ in 5 ml methanol is added as a separate stream. The reaction mixture is refluxed for about 2 hours and is then poured into 40 ml $CH_2Cl_2$ and 80 ml water. The aqueous layer is extracted once with 20 ml $CH_2CL_2$. The combined organic layers are washed with three 25 ml portions of water and one 25 ml portion of 50 percent aqueous $NaHCO_3$ solution and then are dried over $Na_2SO_4$. Removal of the solvent gives 3.9 g of an orange liquid. Distillation gives 3.0 g of methyl 2-(4-hydroxyphenoxy)propanoate.

Example 2—4-Methoxyphenol

To a solution of 13.6 g 4-methoxybenzaldehyde and 1.1 equivalents 50 percent $H_2O_2$ in 55 ml methanol at about 20° C. is added 0.10 equivalent of 98 percent $H_2SO_4$. The mixture is refluxed for about 1.5 hours, then $Na_2SO_3$ is added to destroy excess $H_2O_2$. Then, $NaHCO_3$ is added to neutralize any acid. The solvent is removed under reduced pressure. The resulting solid is taken up in about 50 ml $CH_2Cl_2$, is dried over $Na_2SO_4$, and is filtered. The sol-vent is removed under reduced pressure from the filtrate giving approximately a 94 mole percent yield of 4-methoxyphenol as is determined by nuclear magnetic resonance and gas chromatography.

As previously mentioned, the preceding examples serve only to illustrate the invention and its advantages, and they should not be interpreted as limiting since further modifications of the disclosed invention will be apparent to those skilled in the art. All such modifications are deemed to be within the scope of the invention as defined by the following claims.

What is claimed is:

1. A process comprising contacting an acylaromatic ether with an oxidizing agent in the presence of a catalytic amount of an acid catalyst under reaction conditions such that the corresponding hydroxyaromatic ether is produced.

2. The process of claim 1 wherein the acylaromatic ether is represented generally by the formula:

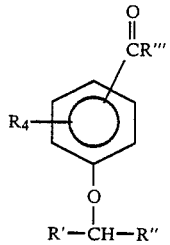

wherein each R is independently H, halo, nitro, alkoxy, —CN, or lower alkyl; R' is H, lower alkyl, alkoxy or —CN; R''' is H or lower alkyl; and R'' is H, lower alkyl, —CN or carboxyl, the carboxyl moiety being represented generally by the formula:

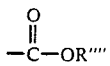

wherein R'''' is H, lower alkyl or a glycol ether.

3. The process of claim 2 wherein the oxidizing agent is hydrogen peroxide.

4. The process of claim 2 wherein R'' is carboxyl, R' is lower alkyl, and R and R''' are H.

5. The process of claim 4 wherein R' and R'''' are methyl.

6. The process of claim 2 further comprising a solvent.

7. The process of claim 2 wherein the temperature is in the range of from about the freezing point to about the boiling point of the reaction mixture.

8. The process of claim 2 wherein from about 0.5 to about 5 equivalents of oxidizing agent are employed per mole of acylaromatic ether.

9. The process of claim 2 wherein the $H_2O_2$ is employed as an aqueous solution.

10. The process of claim 2 wherein from about 0.001 to about 1 equivalent of acid is employed per mole of acylaromatic ether.

11. The process of claim 2 wherein R, R', R'' and R''' are H.

12. A process comprising contacting methyl 2-(4-formylphenoxy)propanoate with aqueous $H_2O_2$ in the presence of an acid catalyst under reaction conditions such that methyl 2-(4-hydroxyphenoxy)propanoate is formed.

13. The process of claim 12 wherein the process is conducted in a solvent.

14. The process of claim 13 wherein the acid catalyst is $H_2SO_4$.

15. The process of claim 13 wherein the solvent is a compound which contains at least one oxygen atom.

16. A process comprising contacting 4-methoxybenzaldehyde with $H_2O_2$ in the presence of an acid catalyst under reaction conditions such that 4-methoxyphenol is formed.

17. The process of claim 16 wherein the $H_2O_2$ is aqueous $H_2O_2$.

18. The process of claim 17 wherein the process is conducted in a solvent.

19. The process of claim 18 wherein the acid catalyst is $H_2SO_4$.

20. The process of claim 18 wherein the solvent is a compound which contains at least one oxygen atom.

* * * * *